United States Patent [19]

Hwang

[11] Patent Number: 4,970,498
[45] Date of Patent: Nov. 13, 1990

[54] CYLINDRICAL ALARM-FUNCTIONED ACCESSORY DEVICE FOR INTRAVENOUS INFUSION PROCEDURE

[76] Inventor: Feng-Lin Hwang, No. 21, Pa Te Rd., Chi Tu District, Keelung City, Taiwan

[21] Appl. No.: 359,544
[22] Filed: Jun. 1, 1989
[51] Int. Cl.⁵ .............................................. G08B 21/00
[52] U.S. Cl. ........................... 340/624; 128/DIG. 13; 73/308
[58] Field of Search ............... 604/254; 128/DIG. 13; 340/623, 624, 618, 693; 73/307, 308

[56] References Cited

U.S. PATENT DOCUMENTS 4,244,364 1/1981 Grushkin ............................ 604/254
4,794,379 12/1988 Wang ..................................... 340/624

Primary Examiner—Joseph A. Orsino
Assistant Examiner—Jeffery A. Hofsass
Attorney, Agent, or Firm—Browdy and Neimark

[57] ABSTRACT

A cylindrical alarm-functioned accessory device for intravenous infusion procedure comprising a cylindrical body connected through a drip tube to receive fluid from a fluid bottle thereinto, an enclosed cylindrical float which senses the condition of a fluid pool formed in the cylindrical body, and a contact-type switch extending into the cylindrical body with connection to a sound and light alarm assembly. As the bottled fluid drains, the cylindrical float descends according to the descending of the fluid pool, pressing against the contact-type switch to activate the alarm assembly.

2 Claims, 3 Drawing Sheets

4,970,498

CYLINDRICAL ALARM-FUNCTIONED ACCESSORY DEVICE FOR INTRAVENOUS INFUSION PROCEDURE

FIELD OF THE INVENTION

This invention is concerned with a cylindrical alarm-functioned accessory device for an intravenous infusion procedure, comprising a cylindrical body having a drip tube to initiate the fluid from a fluid bottle thereinto, an enclosed cylindrical float entirely sealed and with weight to position it within the fluid pool formed in the cylindrical body, and a contact-type switch extending into the cylindrical body in connection to an alarm system with an associated housing mounted externally of the cylindrical body. As the fluid drains away, the cylindrical float descends within the fluid pool as the supply diminishes, pressing the contact-type switch to produce an alarm signal. With this accessory device, nurses or hospital orderlies can be alerted in time before a fluid is consumed, and the patient's safety can be ensured. Also, the quality of medical attention is enhanced to some degree.

BACKGROUND OF THE INVENTION

Usually, intravenous infusion makes use of a large volume of fluid so that completing that procedure requires long tiring hours. In the general case, a nurse or hospital orderly departs just after the beginning of intravenous infusion is started and returns only one or two times to see the progressing condition. If there is some other thing distracting the nurse's attention and a failure to attend before fluid depletion, there is very likely to be air entering the vessel to endanger the patient. That possibility is a cause of fear, leading patients to keep awake as much as they can, consistently watching the fluid bottle, no matter how tired they feel and require a good rest or sleep.

OBJECT OF THE INVENTION

In view of the above-mentioned problem, this invention provides a cylindrical accessory device having an automatic alarm system for intravenous infusion procedure. As a fluid is being used up, the fluid pool which is formed in the cylindrical accessory device descends as the supply decreases and, at the same time, the cylindrical float that is entirely sealed and with a weight positioned within the fluid pool descends accordingly, pressing a contact-type switch of an alarm system to call nurses or hospital orderlies to come to attend in time to the patient. With this accessory device, the patient during intravenous infusion can dispense with unnecessary alarm and take a good rest or sleep without any psychological burden.

SUMMARY OF THE INVENTION

A cylindrical alarm-functioned accessory device for intravenous infusion comprises a cylindrical body having a needle-pointed drip tube raised to initiate the fluid thereinto from a raised and inverted fluid bottle, an enclosed cylindrical float entirely sealed, having weight, and has an external part of passages against the inner wall of the cylindrical body for a slow-paced running by of the fluid, positioned within the fluid pool formed in the cylindrical body, and a contact-type switch which connects to a sound and light alarm assembly with a suitable housing mounted externally of the cylindrical body. As the bottled fluid drains and empties and the fluid pool descends as the supply decreases, the cylindrical float therewithin descends accordingly, pressing the contact-type switch to actuate the sound and light alarm system.

BRIEF DESCRIPTION OF THE INVENTION

SPECIFIC DESCRIPTION

Figure 1:
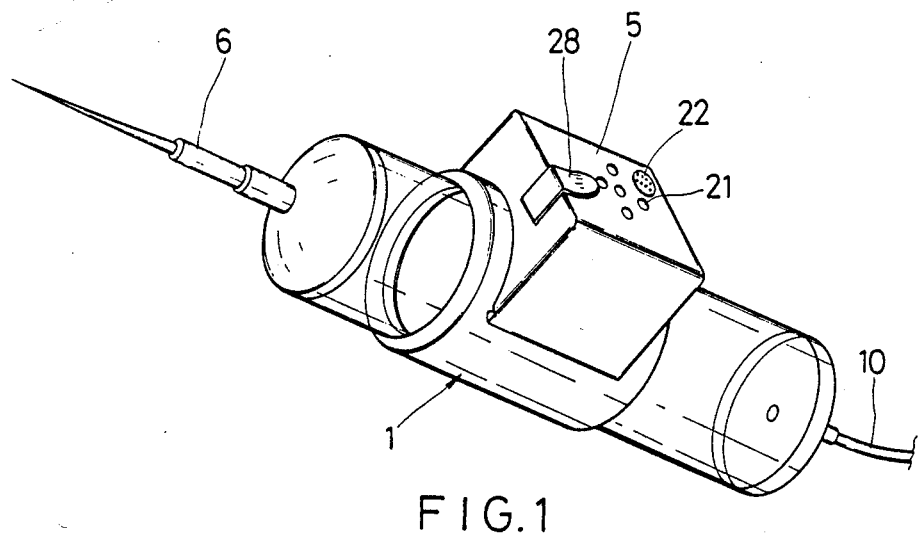
FIG. 1 is a perspective view according to the invention.

From the above said figures it can be seen that this invention comprises a cylindrical body 1, a cylindrical float 2 enclosed therein, a contact-type switch 3 extending into the body 1, a sound and light assembly 4 in a suitable housing 5 mounted externally of cylindrical body 1.

Figure 2:
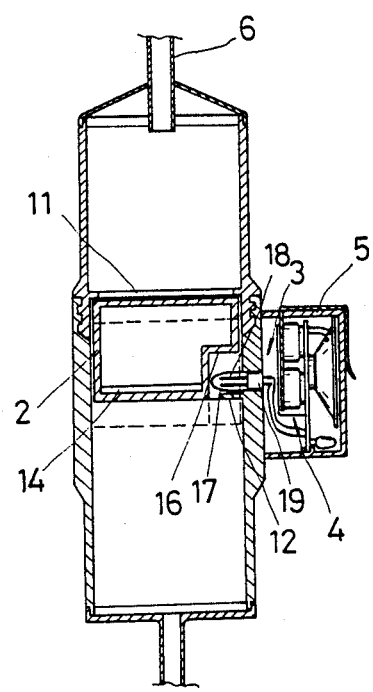
FIG. 2 is a side view of the device of FIG. 1.
Figure 4:
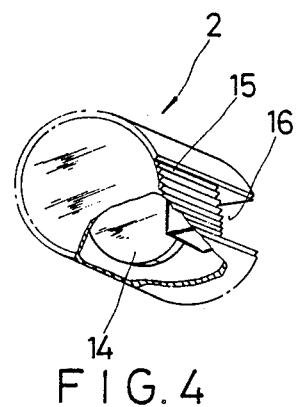
FIG. 4 is a structural view of the cylindrical float of the invention.
Figure 5:
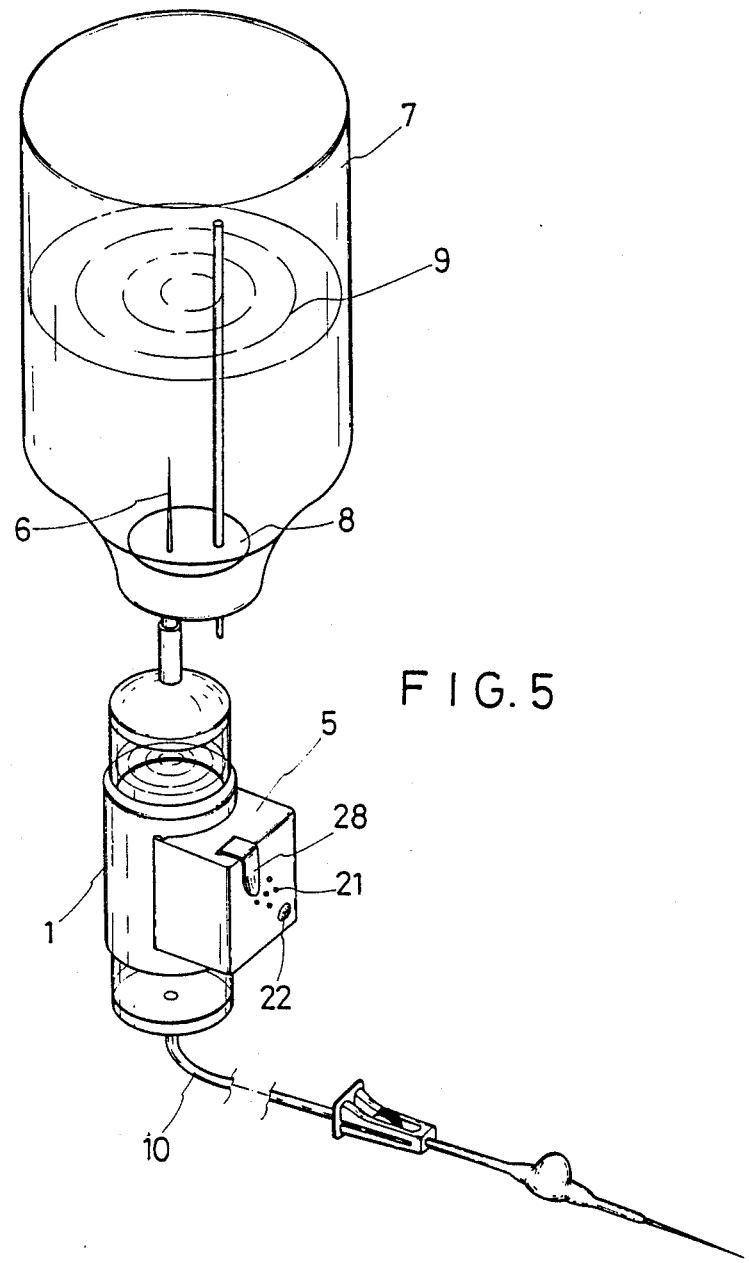
FIG. 5 is a ready-to-use view of the invention.

Now referring to FIGS. 1, 2 and 5, at the top of the cylindrical body 1 is an upwardly projecting drip tube 6, needle-pointed at its upper end, for piercing through a penetrable stopper 8 to an inverted and raised fluid bottle 7 to initiate the flow of fluid 9 therefrom, while at the bottom of cylindrical body 1 is a flexible delivery pipe 10 downwardly projected, which has a suitable coupler connectable to a special fluid delivery pipe having an injection needle, to lead fluid 9 in a flow to a patient. Enclosed in cylindrical body 1 is cylindrical float 2 having a weight element 14 on its floor with float 2 being a hollow and entirely sealed cylinder, of which the outer diameter is adapted to fit in the inner diameter of cylindrical body 1 and a half upper part externally formed with gear-like passages 15 against the inner wall of cylindrical body 1 for fluid 9 running thereby while the half lower half part has an inwardly going form which acts to press part 16 against contact-type switch 3 as cylinder float 2 descends reaching the switch level, as FIG. 4 indicates. And on the inner wall of cylinder body 1, there are an upper flange 11 and lower flange 12 respectively arranged for limiting the up-and-down movement of float 2.

Figure 3:
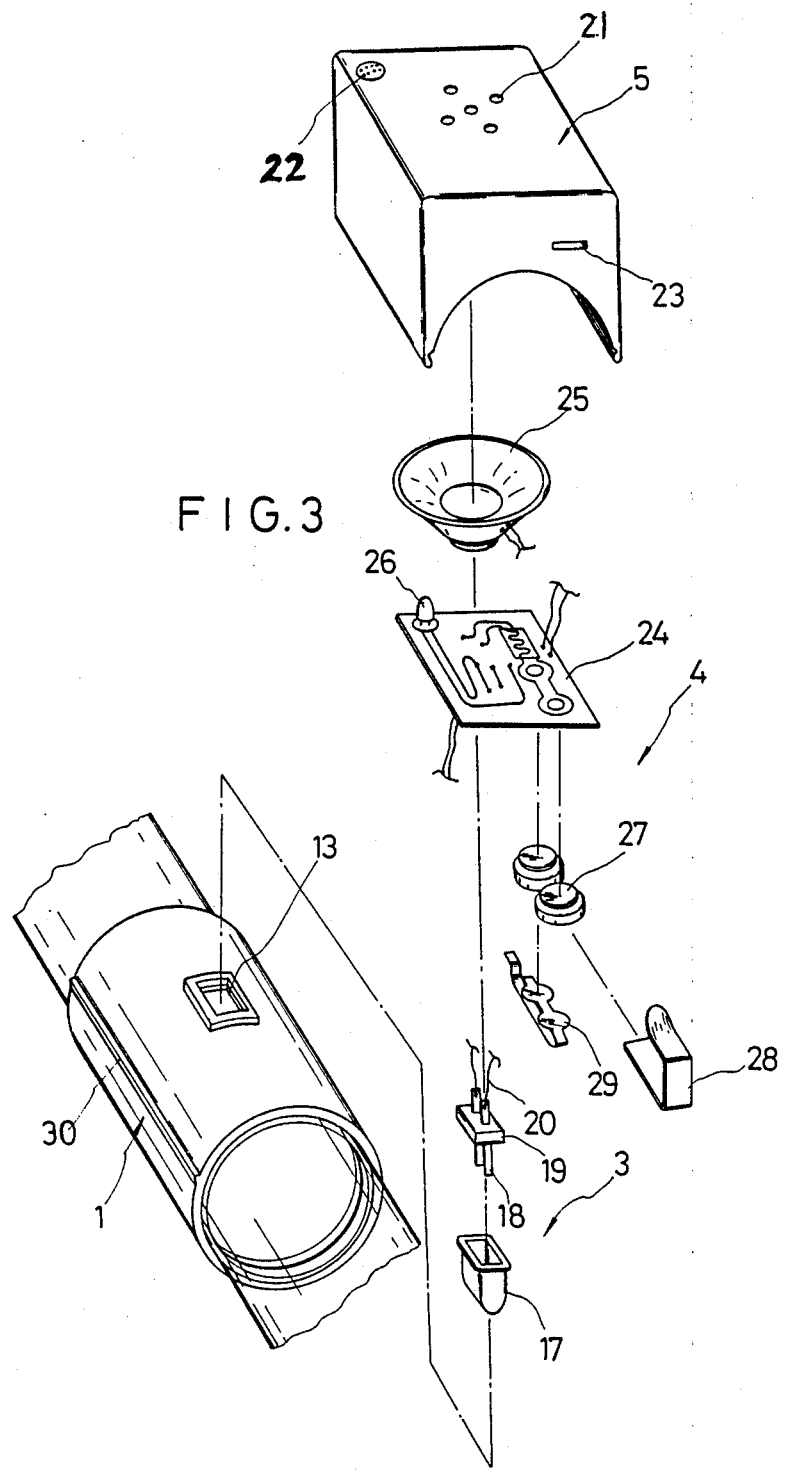
FIG. 3 is an exploded view of the sound and light alarm assembly of the invention along with its associated housing.

As FIG. 3 shows, contact-type switch 3 consists of a waterproof socket 17, contacts 18, and a supporting body 19. Waterproof socket 17 is made from a soft and flexible membrane; supporting body 19 has the resilient contacts 18 fixed therethrough. In waterproof socket 17, the ends of contacts 18 facing outward are provided with conductible lines 20 for connection to the circuit of the alarm assembly 4. And by way of an opening 13, which is positioned within the limited section of movement of cylindrical float 2 in its movement within cylindrical body 1, contact-type switch 3 is positioned extending into cylindrical body 1. As the switch 3 is closed at contacts 18, the battery of alarm assembly 4 will be activated through conduction.

Also as FIG. 3 shows, sound and light alarm assembly 4 comprises an IC circuit board 24, a loudspeaker 25, a light-emitting diode 26, a pair of batteries 27, battery seats 29, and in particular, an inserted piece 28 to be placed between batteries 27 and battery seats 29 preventing conduction such that battery 27 power can be stored and circuit stability of alarm assembly 4 can be maintained during transportation. Upon removal of inserted piece 28, conduction between batteries 27 and battery seats 29 becomes normal and ready again. As to the associated housing 5, it has a light hole 22, sound bores 21 for sending alarm signals without blocking and slot 23 provided for inserting piece 28 as necessary. By means of strap-like fixtures 30, which are externally provided on the cylindrical body 1, the suitably shaped housing 5 is able to mount smoothly to the external sides of cylindrical body 1.

In addition, the above-mentioned contacts 18 attached with conductible lines 20 can make connection to the circuit of the bell assembly in a nurse's lounge instead. With conduction to the battery of the bell assembly, sounds of the bell will alert nurses to go immediately to treat the patient.

As FIG. 5 shows, this invention is operative in connection with an inverted and raised fluid bottle and a special delivery pipe provided with an injection needle. In use, when fluid 9 flows slowly into cylindrical body 1, cylindrical float 2 begins to move up. To test the device, pressing contact-type switch 3, pull out inserted piece 28 from slot 23 to make sure that sound and light alarm signals are activated immediately. If so, the normal conduction of this accessory device is verified and the device can be used with assurance. With fluid 9 continuing to flow into cylinder 1, cylindrical float 2 at last floats away from contact switch 3 and quietness ensues, and intravenous infusion formally gets started. As fluid 9 is emptied from cylinder 1, cylindrical float 2 descends to press against contact switch 3, causing sound and light alarms which call nurses or hospital orderlies to handle the patient and device in time to replace the fluid bottle 9.

I claim:

1. A cylindrical alarm-functioned accessory device for intravenous infusion procedure comprising:

a cylindrical body having an upper and a lower flange arranged to limit the up-and-down movement of a cylindrical float enclosed therein, a suitable opening in the wall within said limited float section of said cylindrical body for the purpose of allowing a contact-type switch thereinto, and strap-like fixtures provided on the external wall of the cylindrical body to enable mounting of an associated housing of an alarm assembly thereto;

a cylindrical float having a weight element included and being a hollow and tightly sealed cylinder, of which the outer diameter is adjacent to the inner diameter of said cylindrical body with the upper half part of the cylindrical float externally formed with gear-like passages against the inner surface of said cylindrical body for a slow-paced running by of a fluid while the lower half part of the cylindrical float has an inwardly going form which acts to press against said contact-type switch as the float descends to the switch level;

said contact-type switch incorporating a waterproof socket, resilient contacts and a supporting body fixing said contacts therethrough, and the ends of said contacts facing outward, which extend into said cylindrical body, the inside of said socket having conductible lines attached to opposite ends of said contacts to connect to the circuit of said alarm assembly, and by way of conduction from contacts to the battery of said alarm assembly warning signals being able to be delivered, and a sound and light alarm assembly having an associated housing which is mounted by means of said strap-like fixtures to the external side of said cylindrical body and on which housing face there are a light hole, sound bores, and a slot, and which said housing has an IC circuit board, a loudspeaker, a light-emitting diode, batteries, and a switch inserting piece incorporated the said switch inserting piece being inserted in said slot between a battery seat and the batteries; with the above-noted assembly members, the sound and light warning signals can be delivered at the time when the injection fluid is going to be depleted.

2. The contacts of contact-type switch as indicated in claim 1, wherein:

the ends of the contacts which face outward inside the waterproof socket have conductible lines attached to connect to the circuit of a bell system in a nurse's lounge through conductible lines.

* * * * *